United States Patent [19]
Levy

[11] Patent Number: 5,683,354
[45] Date of Patent: Nov. 4, 1997

[54] ADHESIVE BANDAGE FOR A DIGIT OF A HUMAN HAND OR FOOT

[76] Inventor: Raymond H. Levy, 976 Rector Rd., Bridgewater, N.J. 08807

[21] Appl. No.: 634,114

[22] Filed: Apr. 17, 1996

Related U.S. Application Data

[63] Continuation of Ser. No. 285,879, Aug. 4, 1994, abandoned, which is a continuation of Ser. No. 87,603, Jul. 6, 1993, abandoned.

[51] Int. Cl.$^6$ ..................................................... A61F 13/10
[52] U.S. Cl. .................... 602/54; 602/52; 602/53; 602/55; 602/58; D24/189; 128/880; 128/893
[58] Field of Search ............................ 602/54, 42, 65, 602/66, 43, 52, 53, 55, 57, 58, 41; D24/189; 128/879, 880, 858, 890, 893

[56] References Cited

U.S. PATENT DOCUMENTS

| | | | |
|---|---|---|---|
| 866,666 | 9/1907 | Mace | 602/58 |
| 1,862,122 | 6/1932 | Schrader | 602/58 X |
| 3,297,028 | 1/1967 | Murray | 602/61 |
| 3,971,374 | 7/1976 | Wagner | 602/58 |
| 5,368,553 | 11/1994 | Newman | 602/58 |
| 5,405,314 | 4/1995 | Ohta | 602/48 |

FOREIGN PATENT DOCUMENTS

| 674811 | 11/1963 | Canada | 128/893 |
|---|---|---|---|

*Primary Examiner*—Danton D. DeMille
*Attorney, Agent, or Firm*—Plevy & Associates

[57] ABSTRACT

An adhesive bandage having a flexible backing element with a generally circular central region and a plurality of salient points radially extending from the central region giving the bandage a generally star-shaped or asterisk-shaped appearance. Wherein, the shape of the bandage helps the bandage protect and cover cuts on flexible parts of the body, such as the fingers and toes, without buckling and exposing the cut to the surrounding environment.

7 Claims, 4 Drawing Sheets

ADHESIVE BANDAGE FOR A DIGIT OF A HUMAN HAND OR FOOT

This is a continuation of application Ser. No. 08/285,879, filed on Aug. 4, 1994, entitled Adhesive Bandage, now abandoned which is a continuation of prior application Ser. No. 08/087,603, filed on Jul. 6, 1993, now abandoned.

BACKGROUND OF THE INVENTION

The present invention relates in general to adhesive bandages of the type used to cover cuts and abrasions on the skin of a person. More particularly, the present invention relates to adhesive bandages that are generally star-shaped to more readily conform to curved areas of the body without crimping, thereby providing improved protection to the cut.

DESCRIPTION OF THE PRIOR ART

Adhesive bandages are commonplace in mostly every household and are used to cover cuts, abrasions and other wounds on the skin as the wounds heal. Adhesive bandages protect skin wounds from dirt and other contaminants that may cause infection. Furthermore, adhesive bandages protect the wound area from reinjury, thereby promoting the rapid healing of the wound. The traditional adhesive bandage, such as those sold under the trademark BANDAID®, are generally rectangular in shape. Such bandages have a central padded region that comes in actual contact with a wound and two areas of adhesive, one either side of the central padding that secures the bandage to the skin. The problem with simple rectangular shaped adhesive bandages is that they are difficult to adhere over curved areas, such as fingers, that move and flex. As a result, rectangular adhesive bandages often buckle and crimp, thereby exposing the wound to the surrounding environment. Similarly, every person is a different size and the cuts obtained by people are also different in size. When a rectangular bandage is applied to a person's finger, it often is difficult to apply the bandage at an angle that fully covers the entire wound. Furthermore, the rectangular bandage, when wrapped around a finger, often constricts the movement of the finger and overlaps itself, thereby preventing the wound from receiving the proper flow of air it needs to heal.

In the prior art, circular bandages are also traditionally used to cover skin wounds. Circular bandages are commonly applied to fingers and toes because circular bandages are less restricting than traditional rectangular bandages. Circular bandages have a central area of padding surrounded by a ring of adhesive. A problem with circular bandages is that when they are applied to a surface, such as a finger that flexes and moves, the circular bandage often buckles and parts of the adhesive ring pull away from the skin. As a result, the seal around the wound is compromised and the wound is exposed to contaminants. Similarly, as parts of the adhesive ring are pulled away from the skin, the adhesive bond holding the bandage in place looses its adhesive strength and leaves the bandage vulnerable to being accidentally pulled away from the wound.

Recognizing the deficiencies of traditional rectangular and circular adhesive bandages, alternatively shaped bandages have been invented in the prior art record. Consider, for instance, U.S. Pat. No. 3,529,597 to Fuzak, entitled FINGERTIP BANDAGE, and U.S. Pat. No. 4,913,138 to Yoshida, entitled ADHESIVE BANDAGE FOR PERSONAL USE. In such prior art references, the bandage provided is shaped to cover a cut either on the face of the finger or at a point on top of the finger. Neither reference is well adapted to cover cuts on the highly contoured sides of a finger. It is well known that cuts on the fingers or toes often occur at the corners of the fingernail bed or the toenail bed where the fingernail or toenail grows out of the skin. It is at this juncture that fissures, cracks and splits in the skin often occur. It is also at this juncture that cuts and infections from ingrown fingernails or toenails also commonly occur. When applying a prior art bandage to the corner of a fingernail or toenail, the bandage must traverse the change in contours between the skin proximate the nail bed and the nail itself. Furthermore, the bandage must wrap around the sides of the finger or toe and be able to flex with the finger or toe without lifting away from the cut at the corner of the nail bed. When a traditional rectangular shaped bandage is applied to the corner of a nail bed, the shape of the bandage prevents the bandage from providing a full seal around the change in contours surrounding the cut. Furthermore, as a finger is flexed, a rectangular bandage trends to buckle at the point of lowest adhesion to the skin, i.e., over the cut, thereby exposing the cut to dirt and other contaminants. When a traditional round bandage is applied to the corner of a nail bed, a small bandage must be used in order to prevent the bandage from buckling as it wraps around the sides of the finger or toe. If the bandage did wrap around the side of a finger or toe, the bandage would buckle as the finger or toe is flexed and would expose the cut being protected. The use of a small bandage results in a small area of adhesion and a small area of protection for a cut. Consequently, a round bandage has many disadvantages in covering cuts at the corner of the nail bed.

It is therefore a primary objective of the present invention to provide an adhesive bandage that is specifically designed to protect a wound on a flexible part of the body without exposing the wound when flexed or restricting the movement of the body.

It is therefore object of the present invention to provide adhesive bandage specifically designed to cover and protect a cut that exists at the corner of the nail bed in either a finger or toe.

SUMMARY OF THE INVENTION

The present invention is an adhesive bandage specifically adapted for use in covering cuts and abrasions of a person's fingers and toes or other body parts that experience a high degree of flexural movement. The adhesive bandage is comprised of a backing element of flexible material having a generally round central area and a plurality of salient points radially extending from the central area giving the bandage a generally star-shaped or asterisk-shaped appearance. A dressing element is affixed to one side of the backing element within the central area of the backing element. The dressing element is smaller than the central area of the backing element, as such the periphery of the central area extends beyond the bounds of the dressing element. Adhesive, capable of adhering to skin, is disposed on the backing element in the peripheral regions of the central area that are not covered by the dressing element. Adhesive is also disposed on the backing element across the length of each salient point.

In a preferred embodiment, the present invention adhesive bandage includes a first set of salient points that extend a predetermined distance beyond the central area and a second set of salient points that extend beyond said central area a distance that is greater than that of the first set of salient points. Furthermore, the two sets of salient points are interposed along the periphery of the central area in an evenly distributed symmetrical pattern. Reliefs may also be formed in the central area on either side of each salient point, wherein the reliefs help prevent the adhesive bandage from buckling and pulling away from the wound it covers, as the bandages is flexed.

BRIEF DESCRIPTION OF THE DRAWINGS

For a better understanding of the present invention, reference is made to the following description of two exemplary embodiments thereof, considered in conjunction with the accompanying drawings, in which.

DETAILED DESCRIPTION OF THE INVENTION

Although the present invention can be used on many different parts of the body where it is desirable to cover a wound with an adhesive bandage, the present invention adhesive bandage is especially suitable for covering wounds on flexible parts of the body such as fingers and toes. Accordingly, the present invention adhesive bandage will be exemplary described in connection with protecting a wound near the nail base of a finger.

Figure 1:
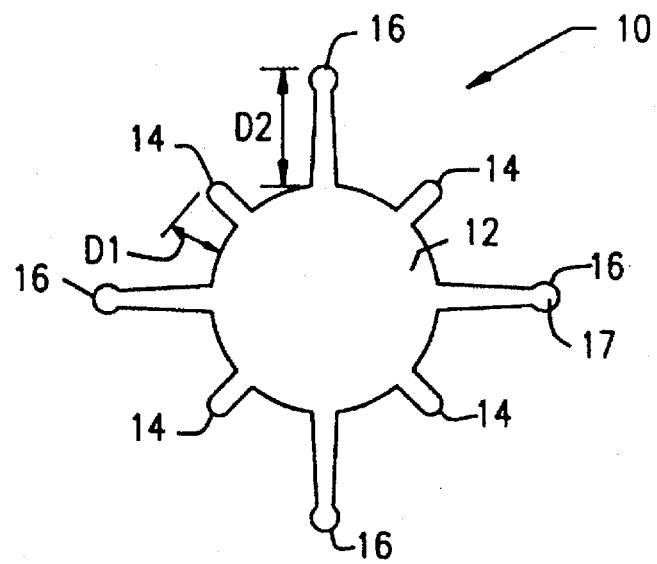
FIG. 1 shows a top plan view of one preferred embodiment of the present invention adhesive bandage.
Figure 2:
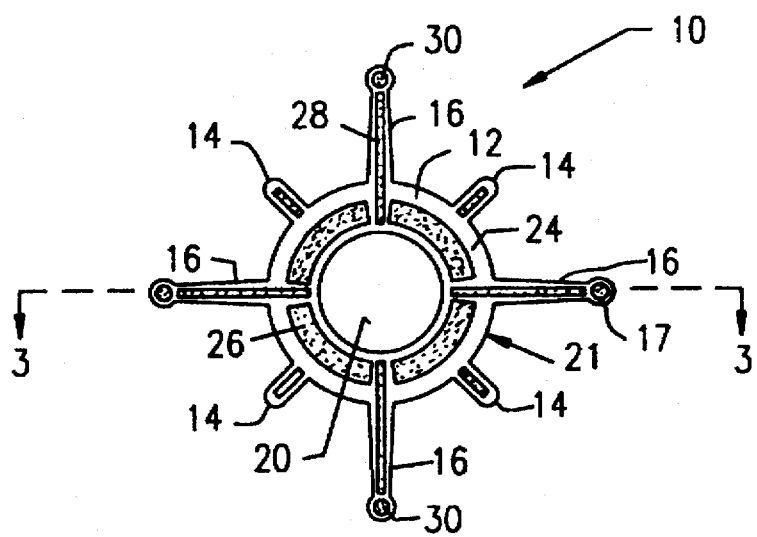
FIG. 2 shows a bottom plan view of the embodiment of FIG. 1.

Referring to FIGS. 1 and 2, one preferred embodiment of the present invention adhesive bandage 10 is shown. The adhesive bandage 10 consists of a generally circular region 12 from which radial extensions emanate. In the shown embodiment, two sets of radial extensions are shown. A first set of four short extensions 14 extend radially from the central circular region 12. Each of the four short extensions 14 are symmetrically positioned and are therefore spaced at 90 degree increments around the central circular region 12. The short extensions 14 each extend beyond the central circular region 12 by a distance D1. A second set of four long extensions 16 also radially extend from the central circular region 12. Each of the long extensions 16 are also symmetrically positioned, being spaced every 90 degrees around the central circular region 12. The long extensions 16 are juxtaposed between the short extensions 14 creating a repeating long-short-long extension pattern around the central circular region 12. Each of the long extensions 16 extend beyond the central circular region 12 by a distance D2 which is generally twice as long as the distance D1 that the short extension extend beyond the central circular region 12. The long extensions 16 may be formed of a uniform thickness. However, in the shown embodiment each of the long extensions 16 terminates at an enlarged head region 17 for a purpose which will be later explained.

Although the described embodiment show the use of four long extensions 16 and four short extensions 14 it will be understood that the shown embodiments are merely exemplary and any plurality of alternating long extensions and short extensions may be used.

Figure 3:
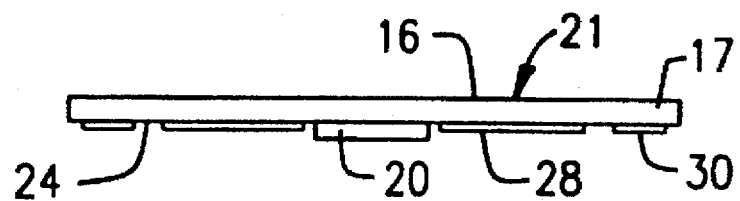
FIG. 3 shows a cross-sectional view of the embodiment shown in FIG. 2, viewed along section line 3—3.

Referring to FIG. 2 in conjunction with FIG. 3, it can be seen that a wound dressing 20 is disposed on one side of the adhesive bandage 10 in the center of the circular region 12. The wound dressing 20 is of the type typically used in conjunction with adhesive bandages and may or may not contain medication to promote the healing of the wound the dressing covers. The wound dressing 20 is adhesively attached to a plastic or material backing 21 that is shaped in the manner previously described, having a circular region 12 and radially extending long extensions 16 and short extensions 14. The backing 21 is of the type typically used in adhesive bandages and may or may not be perforated to allow air flow through the backing 21.

Adhesive is applied to the bottom surface 24 of the plastic backing 21. The adhesive is applied in a circular pattern 26 around the periphery of the wound dressing 20. Similarly, a line of adhesive 28 is applied down the centers of each of the long extensions 16 and the short extensions 14. A small extra spot 30 of adhesive is also applied within the enlarged head region 17 of each of the long extensions 16. The long extensions 16 terminate with an enlarged head region 17 to accept the added amount of adhesive in this region. When manufactured, the adhesive bandage 10 is placed against a non-stick laminate (not shown) that temporarily adheres to the adhesive regions and can be peeled away when the adhesive bandage is ready for use. The use of such peel-away laminates is well known in the art of adhesive bandages.

Figure 4:
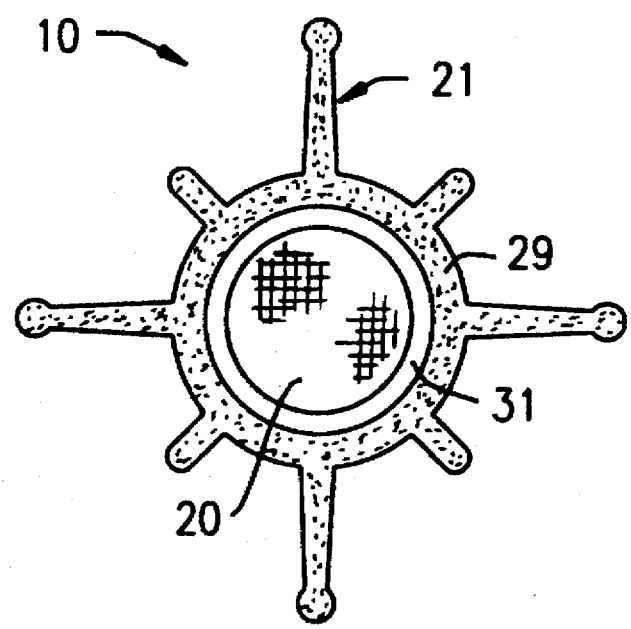
FIG. 4 shows an alternate bottom plan view of the embodiment of FIG. 1.

In FIG. 4 an alternate embodiment is shown for the bottom surface of the plastic backing 21. In this embodiment, adhesive 29 is applied to all points on the plastic backing 21 except for on the wound dressing 20 itself and a small annular region 31 surrounding the wound dressing 20. By applying the adhesive 29 in such a manner, the surface area of the bandage 10 that actually adheres to the skin of a person is increased over the adhesive distribution previously shown in conjunction with FIG. 2.

Figure 5A:
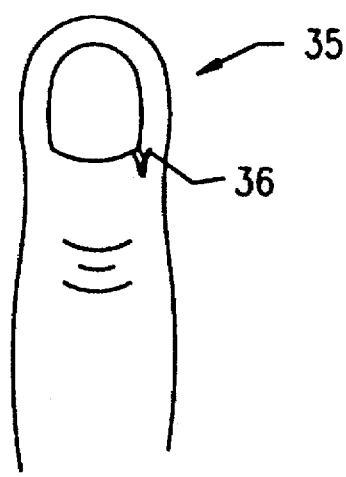
FIG. 5a shows a finger having a cut at its nail bed.
Figure 5B:
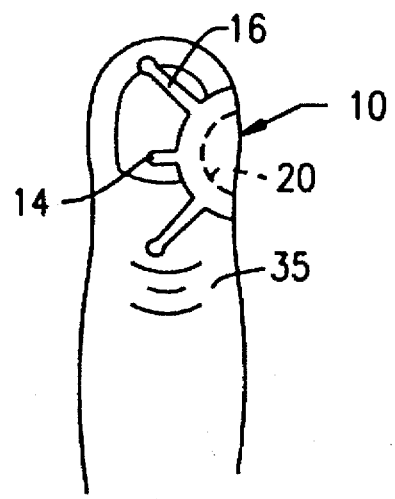
FIG. 5b shows the present invention adhesive bandage applied to the finger previous shown in FIG. 5a so as to cover and protect the cut present on the finger.

In FIG. 5a, there is shown a person's finger 35 having a cut 36 positioned in the corner of the nail bed. Referring to FIG. 5a in conjunction with FIG. 5b, the present invention adhesive bandage 10 is shown applied to the finger 35 previously shown in FIG. 5a. When applied, the wound dressing 20 is placed directly over the cut 36. The adhesive disposed around the wound dressing 20 holds the wound dressing 20 into one set position over the cut 36, and seals the periphery of the wound dressing 20 against the finger 35. The adhesive bond between the bandage 10 and the finger 35 is further reinforced by the presence of the short extensions 14 that radially extend from the center region of the adhesive bandage 10 at 90 degree intervals. The short extensions 14 provide additional finger-to-bandage adhesive bonding near the cut 36, however, the symmetrical positioning of the short extensions 14 prevents the adhesive bandage 20 from buckling and pulling away from the cut 36 as the finger 35 is moved and flexed.

The long extensions 16, due to their size, wrap around the finger 35. As a result, the long extensions 16 adhere to the finger 35 at points far removed from the position of the actual cut 36 itself. Furthermore, the symmetrical positioning of the long extensions 16 also prevent the adhesive bandage 20 from buckling and pulling away from the cut 36 as the finger 35 is moved and flexed. Since the long extensions 16 and the short extensions 14 are evenly disposed and undergo different flexural stresses due their respective lengths, the buckling of the adhesive bandage 10 is minimized while still providing a strong adhesive bond between the finger and the bandage 10. As a result, the present invention adhesive bandage 10 acts to maintain the wound dressing 20 over the cut 36 despite the fact that the adhesive bandage 10 is adhesively coupled to a moving and flexing part of the body.

Figure 6A:
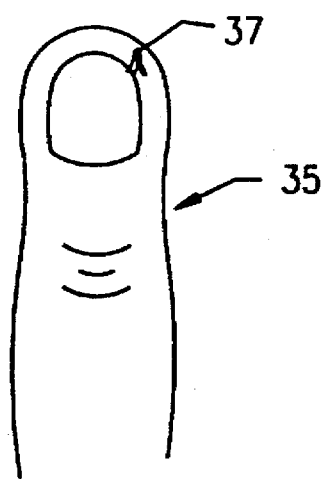
FIG. 6a shows a finger having a cut near the tip of the fingernail.
Figure 6B:
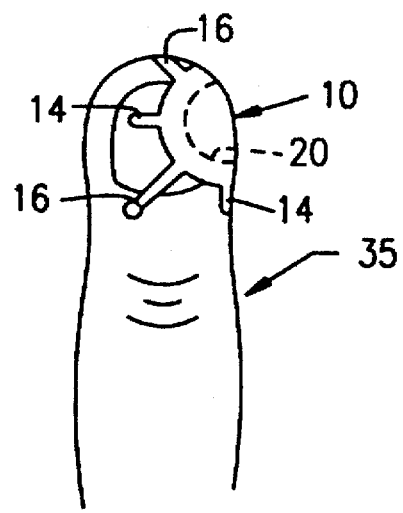
FIG. 6b shows the present invention adhesive bandage applied to the finger previous shown in FIG. 6a so as to cover and protect the cut present on the finger.

Referring to FIGS. 6a and 6b an alternative application is shown where a cut 37 is positioned on a finger 35 near the tip of the finger. In this application, the adhesive bandage 10 is applied over the finger so that the wound dressing 20 is disposed over the cut 37. The adhesive disposed around the wound dressing 20 holds the wound dressing 20 into one set position over the cut 37, and seals the periphery of the wound dressing 20 against the finger 35. The adhesive bond between the bandage 10 and the finger 35 is further reinforced by the presence of the short extensions 14 that radially extend from the center region of the adhesive bandage 10 at 90 degree intervals. The short extensions 14 provide additional finger-to-bandage adhesive bonding near the cut 37.

The long extensions 16, due to their size, wrap around the tip of the finger 35. As a result, the long extensions 16 adhere to the finger 35 at points on either side of the finger that are far removed from the position of the actual cut 37 itself. Since the long extensions 16 and the short extensions 14 are evenly disposed and undergo different flexural stresses due their respective lengths, the buckling of the adhesive bandage 10 is minimized while still providing a strong adhesive bond between the finger and the bandage 10. As a result, the present invention adhesive bandage 10 acts to maintain the wound dressing 20 over the cut 37 despite the fact that the adhesive bandage 10 is adhesively coupled to a moving and flexing part of the body.

Figure 7:
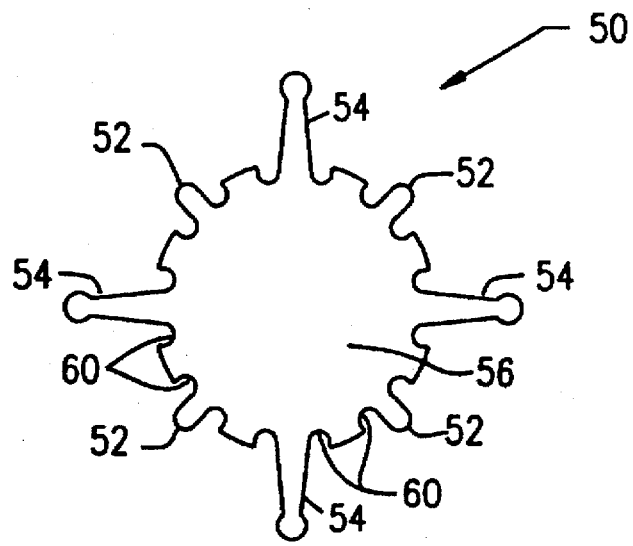
FIG. 7 shows a top plan view of a second preferred embodiment of the present invention adhesive bandage.
Figure 8:
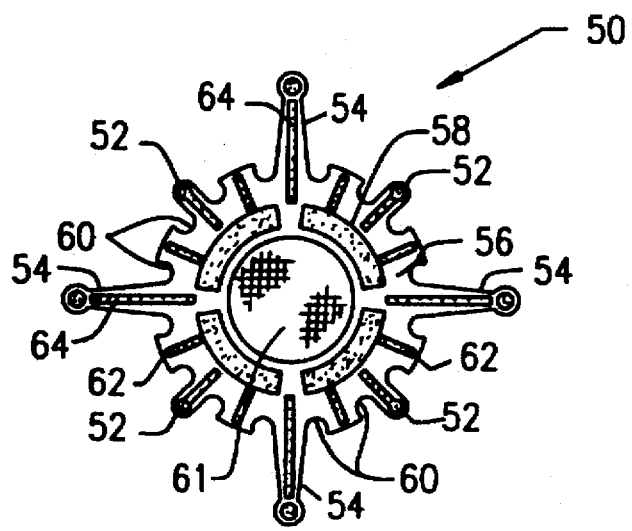
FIG. 8 shows a bottom plan view of the embodiment of FIG. 7.

Referring to FIG. 7 and 8 an alternate embodiment of the present invention adhesive bandage 50 is shown. This embodiment also includes short extensions 52 and long extensions 54 that radially extend from a central circular region 56. However, in the shown embodiment, the diameter of the central circular region 56 extends further beyond the periphery of the wound dressing than in the previous embodiment. To prevent buckling of the central circular region 56, a plurality of reliefs 60 are disposed along the periphery of the central circular region 56. One relief 60 is disposed on either side of the long extensions 54 and the short extensions 52. The reliefs 60 enable the central circular region 56 of the bandage 50 to move with a flexing finger without buckling and exposing the underlying cut to the surrounding environment.

In the shown embodiment, the long extensions 54 taper from a wide base to a narrow distal end as they radially extend away from the central circular region 56. The wider base prevents the long extensions 54 from tearing as they are removed from a peel-away backing and are applied to a finger. From FIG. 8, it can be seen that the adhesive applied to the central circular region 56 of the bandage 50 is applied along a generally circular pathway 58 near the peripheral edge of the central wound dressing 61. Small radial arms 62 of adhesive extend away from the circular pathway 58 and extend into the space between reliefs 60. By positioning the adhesive in such a geometry, the material of the bandage 50 in the area of the reliefs 60 is left unrestricted, thereby enabling the reliefs 60 to flex when the bandage 50 is applied to a finger. Longer strips of adhesive 64 extend down the center of the long extensions 54, as with the previous embodiment, to bond the long extensions 54 to the finger when the adhesive bandage 50 is applied.

Although FIG. 8 shows a distinct pattern to the adhesive applied to the bandage 50, it should be understood that the adhesive could cover all of the bottom surface of the bandage 50 except for the wound dressing 61. By applying the adhesive in such a manner, the surface area of the bandage 50 that actually adheres to the skin of a person is increased over the adhesive distribution previously shown in conjunction with FIG. 8.

It shall be understood that the embodiments described herein are merely exemplary and that a person skilled in the art may make many variations and modifications without departing from the spirit and the scope of the invention. More specifically, it should be understood that the present invention adhesive bandage may include any plurality of short extensions and/or long extensions that help the bandage adhesively attach to the skin. As such, the present invention adhesive bandage is intended to cover most any star-shaped, asterisk-shaped or another multi-spired shape configuration. All such variations and modifications are intended to be included within the scope of this invention as defined by the appended claims.

What is claimed is:

1. An adhesive bandage for a digit of a human hand and foot, comprising:

a backing element of a predetermined thickness having a generally round central area which defines a circular peripheral edge and a plurality of salient points radially extending from said circular peripheral edge, the adhesive bandage symmetric about a plurality of axes, wherein each axis extends through at least one of the salient points and the central area;

a dressing element affixed to a first side of said backing element in said central area, said dressing element having a thickness which is substantially similar to said predetermined thickness of said backing element;

adhesive, capable of adhering to skin, disposed on said first side of said backing element; and a plurality of reliefs disposed along and extending into said backing element from said circular peripheral edge, said salient points and said reliefs define a repeating pattern which includes one of said salient points, one of said reliefs, a portion of said circular peripheral region and another of said reliefs;

whereby when said bandage is applied to a digit of a human hand or foot, said salient points and said reliefs coact to allow said bandage to wrap around the sides of the digit to prevent said backing element from buckling and pulling away from the digit thereby exposing an injury on the digit.

2. The adhesive bandage according to claim 1, wherein said salient points include a first set of salient points that extend a predetermined distance beyond said circular peripheral edge and a second set of salient points that extend beyond said circular peripheral edge a distance which is at least twice that of said predetermined distance.

3. The adhesive bandage according to claim 2, wherein said salient points of said second set terminate with an enlarged head member.

4. The adhesive bandage according to claim 2, wherein each of said salient points of said first set alternate with a salient point of said second set.

5. The adhesive bandage according to claim 2, wherein said first set of salient points and said second set of salient points each include four points equally disposed around said central area.

6. The adhesive bandage according to claim 1, wherein said plurality of salient points includes at least four salient points equally disposed around said central area.

7. The adhesive bandage according to claim 1, wherein said dressing element is medicated.

* * * * *